United States Patent
Wu et al.

(10) Patent No.: US 7,259,277 B2
(45) Date of Patent: Aug. 21, 2007

(54) ADVANCED ROUTE FOR THE SYNTHESIS OF CPLA2 INHIBITORS

(75) Inventors: Yanzhong Wu, Bronx, NY (US); Panolil Raveendrath, Monroe, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/076,117

(22) Filed: Mar. 8, 2005

(65) Prior Publication Data

US 2005/0159613 A1    Jul. 21, 2005

Related U.S. Application Data

(62) Division of application No. 10/896,318, filed on Jul. 21, 2004, now Pat. No. 6,891,065.

(60) Provisional application No. 60/490,005, filed on Jul. 25, 2003.

(51) Int. Cl.
C07C 311/03    (2006.01)
C07C 255/58    (2006.01)

(52) U.S. Cl. .......................... 564/90; 558/413; 564/89

(58) Field of Classification Search ................ 558/413; 564/89, 90
See application file for complete search history.

(56) References Cited

U.S. PATENT DOCUMENTS

| | | | |
|---|---|---|---|
| 5,053,072 | A | 10/1991 | Ort et al. |
| 5,186,736 | A | 2/1993 | Ort et al. |
| 5,324,710 | A | 6/1994 | Ort et al. |
| 5,461,075 | A | 10/1995 | O'Neill et al. |
| 5,877,121 | A | 3/1999 | Andree et al. |
| 6,159,903 | A | 12/2000 | Linker et al. |
| 6,339,044 | B1 | 1/2002 | Andree et al. |
| 6,635,771 | B2 | 10/2003 | McKew et al. |
| 6,656,971 | B2 | 12/2003 | Wu et al. |
| 6,797,708 | B2 | 9/2004 | McKew et al. |
| 6,812,236 | B2 | 11/2004 | Gibson et al. |
| 6,812,252 | B2 | 11/2004 | Ikawa et al. |
| 6,891,065 | B2 | 5/2005 | Wu et al. |
| 6,984,735 | B2 | 1/2006 | McKew et al. |
| 2002/0127605 | A1 | 9/2002 | Hamilton et al. |
| 2003/0144282 | A1 | 7/2003 | McKew et al. |
| 2003/0149029 | A1 | 8/2003 | McKew et al. |
| 2003/0158405 | A1 | 8/2003 | McKew et al. |
| 2003/0166649 | A1 | 9/2003 | McKew et al. |
| 2004/0082785 | A1 | 4/2004 | McKew et al. |
| 2004/0242456 | A1 | 12/2004 | Luthy et al. |
| 2005/0020858 | A1 | 1/2005 | Wu et al. |
| 2005/0049296 | A1 | 3/2005 | Dehnhardt et al. |
| 2005/0070723 | A1 | 3/2005 | Dehnhardt et al. |
| 2005/0148770 | A1 | 7/2005 | Michalak et al. |
| 2005/0159613 | A1 | 7/2005 | Wu et al. |
| 2006/0014759 | A1 | 1/2006 | McKew et al. |

FOREIGN PATENT DOCUMENTS

| | | |
|---|---|---|
| EP | 0401903 A2 | 5/1990 |
| JP | 02115157 | 4/1990 |
| WO | WO91/06541 A1 | 5/1991 |
| WO | WO93/15047 A1 | 8/1993 |
| WO | WO95/17391 A1 | 6/1995 |
| WO | WO96/07647 A1 | 3/1996 |
| WO | WO97/05117 A1 | 2/1997 |
| WO | WO97/26248 A1 | 7/1997 |
| WO | WO97/30980 A1 | 8/1997 |
| WO | WO 02/20487 A1 | 3/2002 |
| WO | WO 02/44126 A2 | 6/2002 |

(Continued)

OTHER PUBLICATIONS

Agnola et al., Solid-Phase Synthesis of Indoles Using the Palladium-Catalysed Coupling of Alkynes with Iodoaniline Derivatives, Tetrahedron Letters,(1997), vol. 38, No. 13, pp. 2307-2310.

(Continued)

Primary Examiner—Shailendra Kumar
(74) Attorney, Agent, or Firm—Fish & Richardson P.C.

(57) ABSTRACT

A process for making a compound of formula (I)

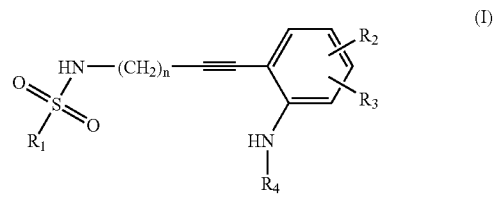

in which process the compound $HC{\equiv}C{-}(CH_2)_n{-}NH_2$ is reacted with the compound $R_1{-}SO_2Cl$ to produce an intermediate compound, which intermediate compound is then reacted with the compound of formula

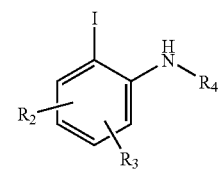

to produce the compound of formula (I), and compounds produced by the process of this invention. The terms $R_1$, $R_2$, $R_3$, $R_4$ and n have the definitions set forth in the specification.

17 Claims, No Drawings

FOREIGN PATENT DOCUMENTS

| WO | WO 02/059080 A2 | 8/2002 |
|---|---|---|
| WO | WO 03/022051 A1 | 3/2003 |
| WO | WO 03/048122 A2 | 6/2003 |
| WO | WO 2005/012238 | 2/2005 |

OTHER PUBLICATIONS

Appleton et al., A Mild and Selective C-3 Reductive Alkylation of Indoles, Tetrahedron Letters, (1993), vol. 34, No. 9, pp. 1529-1532.

Deng et al., Synthesis and Characterization of Poly(N-propargylsulfamides), Macromolecules,(2004), vol. 37, No. 15, pp. 5538-5543.

Nilsson, B. et al, Derivates of the Muscarinic Agent N-Methyl-N-(methyl-4-pyrrolidino-2-butynyl)acetamide, J. Med. Chem. (1988), vol. 31, pp. 577-582.

Fujiwara, J. et al, Nucleophilic Aromatic Substitution by Organoaluminum Reagents, J. Am. Chem. Soc., (1983) vol. 105, pp. 7177-7179.

International Search Report for International application No. PCT/US2004/023247.

Database Caplus Chemical Abstracts Service, Columbus, Ohio, US; database accession No. 1990-532816.

Chung J. et al., "A Practical Synthesis of Fibrinogen Receptor Antagonist MK-383. Selective Functionalization of (S)-Tyrosine", Tetrahedron Letters (1993), vol. 49, No. 26, pp. 5767-5776, Pergamon Press Ltd., printed in Great Britain.

Ezquerra J. et al., "Efficient reagents for the Synthesis of 5-, 7-, and 5, 7-Substituted Indoles Starting from Aromatic Amines: Scope and Limitations", J. Org. Chem., vol. 61, 1996, 5804-5812.

Gandolfi C. et al., "N-Acyl-2-substituted-1,3-thiazolidines, a New Class of Non-narcotic Antitussive Agents; Studies Leading to the Discovery of Ethyl 2-[(2-Methoxyphenoxy)methyl]-β-oxothiazolidine-3-propanoate", J. Med. Chem. (1995), 38, pp. 508-525.

Hoffmann K. et al., "Fibrin-Stabilizing Factor Inhibitors. 12. 5-Dibenzylaminopentylamine and Related Compounds, a New Type of FSF Inhibitors", Journal of Medicinal Chemistry (1975), vol. 18, No. 3, pp. 278-284.

Iyer S. et al., "Regiospecific Synthesis of 2-Methoxy-3-methyl-1,4-benzoquinones from Maleoylcobalt Complexes and Alkynes via Lewis Acid Catalysis. A Highly Convergent Route to Isoquinoline Quinones", J. Am. Chem. Soc. (1987), 109, pp. 2759-2770.

Orazi O. et al., "Synthesis of Fused Heterocycles: 1,2,3,4-Tetrahydroisoquinolines and Ring Homologues via Sulphonamidomethylation", J. Chem. Soc. Perkin Trans. I (1986), pp. 1977-1986.

Pierce et al., "Practical Asymmetric Synthesis of Efravirenz (DMP 266), and HIV-1 Reverse Transcriptase Inhibitor", J. Org. Chem. (1998), vol. 63, pp. 8536-8543.

Sakamoto T et al., "Condensed Heteroaromtic Ring Systems, XIII. One-Step Synthesis of 2-Substituted 1-Methylsulfonylindoles from N-(2-Halopenyl)methanesulfonamides" Chem. Pharm. Bull. (1998), 36(4) pp. 1305-1308.

Shin K. et al., "An Expeditious Synthesis of 2,2'-Biindolyl", Synlett (1995) Aug. pp. 859-860.

Taylor E. et al., Novel 5-Desmethylene Analogues of 5, 10-Dideaza-5,6,7,8-tetrahydrofolic Acid as Potential Anticancer Agents:, J. Org. Chem. (1992), 57, pp. 3218-3225.

Villemin et al., "Palladium Homogenous and Supported Catalysts: Synthesis and Functional Acetylenics and Cyclisation to Heterocycles" Heterocycles (1989), vol. 29, No. 7, pp. 1255-1261.

Watson, S.E., et al., "Novel Methodology for the Preparation of 5-Substituted Tetrahydro[2,3-D]Pyrimidines", Synthetic Communications (1998), 28(1), pp. 1897-1905.

Xiao et al., Regioselective Carbonylative Heteroannulation of o-Iodothiophenols with Allenes and Carbon Monoxide Catalyzed by a Palladium Complex: A Novel and Efficient Access to Thiochroman-4-one Derivatives, J. Org. Chem. (1999), vol. 64, pp. 9646-9652.

Ziegler et al., "The Preparation of Alkanesulfonyl Halides", From the Department of Organic Chemistry, Research Division, Sharp and Dohme, Inc., 1951, vol. 16, pp. 621-625.

Written Opinion of the International Searching Authority for International Application No. PCT/US2005/029338, 6 pages, 2005.

International Search Report for International Application No. PCT/US2005/029338, 4 pages, 2005.

ADVANCED ROUTE FOR THE SYNTHESIS OF CPLA2 INHIBITORS

This application is a divisional application of U.S. Ser. No. 10/896,318, filed Jul. 21, 2004, now U.S. Pat. No. 6,891,065, which claims the benefit of U.S. Provisional Patent Application No. 60/490,005, filed Jul. 25, 2003, the entire disclosures of which are hereby incorporated by reference.

FIELD OF THE INVENTION

This invention relates to the preparation of inhibitors of the enzyme cytosolic phospholipase $A_2$ (cPLA$_2$).

BACKGROUND OF THE INVENTION

Compounds which inhibit cytosolic phospholipase $A_2$ and a process for making those compounds have been disclosed in U.S. Patent Publication No. 2003-0144282 A1, filed Nov. 22, 2002, the disclosure of which is incorporated by reference herein. These compounds are useful for a variety of purposes, including the relief of pain and inflammation. In order to bring a drug to market, it is necessary to have an economically feasible process for making the compound. Often, a process that works in the laboratory is not practical from a commercial standpoint. It would be desirable to have a relatively inexpensive and efficient method for making at least some of the aforesaid compounds.

Appleton, et al., in *Tetrahedron Lett.* 1993, 34, 1529, teach reductive C-3 alkylation of 3-unsubstituted indoles to produce C-3 functionalized indoles, especially 3-(arylmethyl)indoles and 3-(heteroarylmethyl)indoles. In the reference reaction, the initial indole is reacted with an aldehyde or ketone using triethylsilane and trifluoroacetic acid.

A solid-phase synthesis of indoles using palladium-catalyzed coupling of alkynes with iodoaniline derivatives is described by Fagnola, et al., *Tetrahedron Letters,* 38(13), 2307–2310 (1997).

SUMMARY OF THE INVENTION

The present invention comprises a process for making a compound of formula (I)

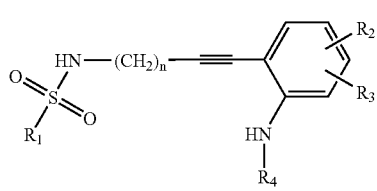

wherein:
n is an integer in the range of 0–10;
$R_1$ represents a straight or branched $C_1$–$C_{10}$ alkyl group, or —CH$_2$-phenyl wherein the phenyl ring optionally has up to two substituents independently selected from the group consisting of $C_1$–$C_4$ alkyl, $C_1$–$C_4$ alkoxy, halogen, and nitrile, each alkyl and alkoxy being optionally substituted by from one to the maximum number of halogen atoms;
$R_2$ and $R_3$ are each independently selected from the group consisting of H, halogen, nitrile, $C_1$–$C_4$ alkyl, and $C_1$–$C_4$ alkoxy; and $R_4$ represents a straight or branched $C_1$–$C_{10}$-alkyl group,

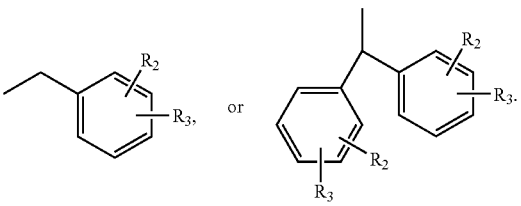

The process comprises reacting the compound HC≡C—(CH$_2$)$_2$—NH$_n$ where n represents an integer from 0–10, or a salt form thereof, preferably an HCl salt thereof, under mildly alkaline conditions, preferably in a solution of potassium carbonate, with the compound $R_1$—SO$_2$Cl to produce the intermediate compound of formula (II)

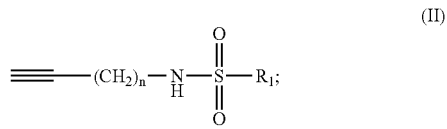

and then reacting the compound of formula (II) with the compound of formula

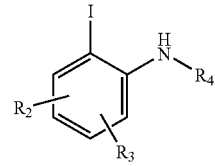

preferably in the presence of a catalyst.

The compound of formula (I) may be cyclized by heating, preferably in NMP in the presence of a catalytic amount of CuI, to form a compound of formula (III)

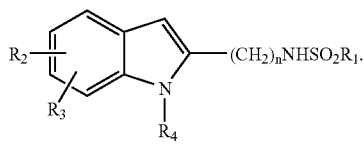

The compound of formula (III) may be reacted with a compound of formula O=CH—$R_5$ in the presence of a reducing agent under acidic conditions, where $R_5$ is —(CH$_2$)$_m$—X-phenyl-C(O)OR$_6$, m is an integer in the range of 1–4, X is O or CH$_2$, and $R_6$ is $C_1$–$C_4$ alkyl, to form a compound of formula (IV)

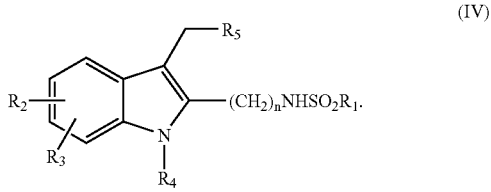

The compound of formula (IV) may be reacted with LiOH in THF, methanol and water to convert $R_5$ to $R_7$, where $R_7$ is —$(CH_2)_m$—X-phenyl-C(O)OH.

The present invention further comprises compounds of formulae (I) and (II).

Various advantages and objects of the present invention will be apparent to those skilled in the art from the description below and from the appended claims.

DETAILED DESCRIPTION OF THE PREFERRED EMBODIMENTS

This invention provides a novel process for making various compounds in the synthesis of a class of substituted indoles which are useful as inhibitors of $cPLA_2$. These $cPLA_2$ inhibitors include, for example, 4-[3-[5-chloro-2-[2-[[[(3,4-dichlorophenyl)-methyl]-sulfonyl]amino]ethyl]-1-(diphenylmethyl)-1H-indol-3-yl]propyl]benzoic acid and 4-[2-[5-chloro-2-[2-[[[(3,4-dichlorophenyl)methyl]-sulfonyl]amino]ethyl]-1-(diphenylmethyl)-1H-indol-3-yl]ethoxy]benzoic acid, as well as many other compounds. They are useful for relieving pain and inflammation associated with a variety of conditions or disease states.

In the process of this invention, n may be an integer in the range of 0–10, but is preferably 0–4 and most preferably is 1, 2, or 3. $R_1$ is preferably —$CH_2$-phenyl, wherein the phenyl ring optionally has up to two substituents independently selected from the group consisting of $C_1$–$C_4$ alkyl, $C_1$–$C_4$ alkoxy, halogen, and nitrile, each alkyl and alkoxy group being optionally substituted by from one to the maximum number of halogen atoms. More preferably, the substituents are halogen, alkyl or perfluoroalkyl. Especially preferred $R_1$ groups include 3,4-dichlorophenylmethyl, 2,6-dimethylphenylmethyl and 2-(trifluoromethyl)phenylmethyl. $R_2$ and $R_3$ are preferably H, F, Cl, or Br. $R_4$ is preferably a benzhydryl group, especially an unsubstituted benzhydryl group. Preferably, $R_6$ is methyl or ethyl and m is 2. Examples of highly preferred $R_5$ groups include —$(CH_2)_2$—O-(p-)phenyl-C(O)OCH$_3$ and —$(CH_2)_3$-(p-)phenyl-C(O)OC$_2$H$_5$.

In the reaction of the alkynylamine and the sulfonylchloride to form a compound of formula (II), it is highly preferred to use a solution of $K_2CO_3$ in THF and water. However, other suitable bases or solvents may be used. Those skilled in the art will readily be able to determine which solutions are suitable in carrying out this reaction.

In reacting the compound of formula (II) with the substituted 2-iodophenylamine compound, a suitable catalyst is preferably employed. Preferably, the catalyst is CuI and/or dichlorobis(triphenylphosphine)palladium (II). It is preferable to carry out the reaction in a solvent such as THF, or the like.

In one preferred aspect of the invention, the compound of formula (I) may be converted to a compound of formula (III) by heating, preferably in the presence of a catalyst such as CuI in a solvent such as N-methylpyrrolidinone. Other suitable catalysts and/or solvents known to those skilled in the art may also be employed. The compound of formula (I) suitably may be heated to approximately 100–140° C., preferably to about 120° C., until the conversion to an indole compound is completed.

In a further aspect of the invention, the compound of formula (III) is reacted with an aldehyde of formula $R_5CHO$ in the presence of a reducing agent to make a compound of formula (IV). Preferably, this reaction takes place in an acidic solvent system. Suitable solvent systems include mixtures of a halogenated acid such as chloroacetic acid, di or trichloroacetic acid, trifluoroacetic acid and/or a Lewis acid such as boron trifluoride and dichloromethane, preferably with trifluoroacetic acid. Suitable reducing agents include triethylsilane, or the like. Those skilled in the art will readily be able to identify other suitable solvent systems and reducing agents to use in the practice of this invention.

The compound of formula (IV) may be converted from an ester to an acid by any means known in the art. A preferred method is to react the ester with LiOH in THF, methanol and water to produce a compound of formula (V)

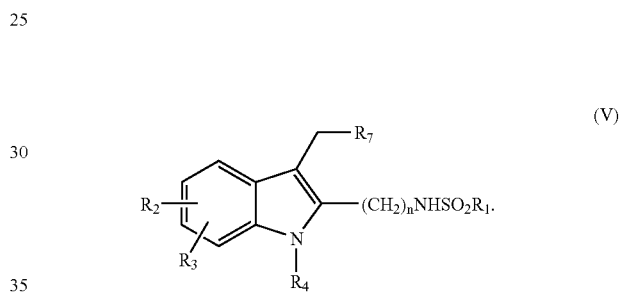

This invention provides a method for making a wide variety of C-2 and C-3 substituted indole compounds, such as compounds of formulae (III), (IV) and (V), shown above. Scheme 1 illustrates various preferred aspects of this invention. In Scheme 1 below, the terms n, $R_1$, $R_2$, $R_3$, $R_4$, $R_5$ and $R_7$ have the definitions set forth above, THF refers to tetrahydrofuran, NMP refers to N-methylpyrrolidinone and TFA refers to trifluoroacetic acid.

Scheme 1

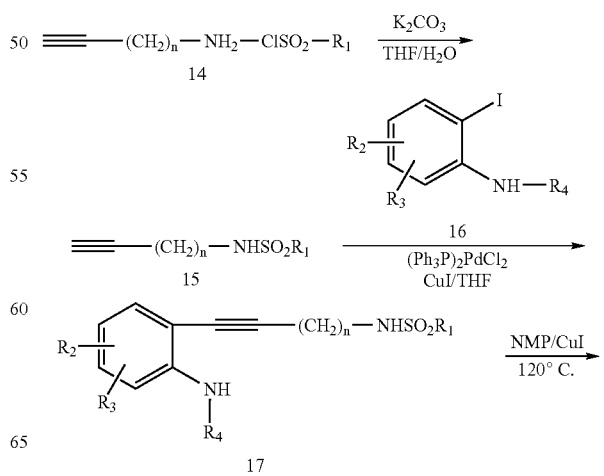

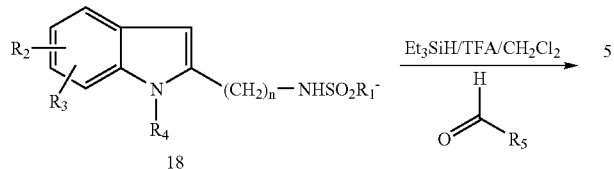
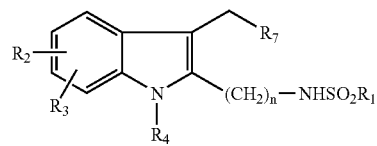
Scheme 2 illustrates a highly preferred embodiment of the present invention, providing a relatively short synthesis for 4-[3-[5-chloro-2-[2-[[[(3,4-dichlorophenyl)methyl]-sulfonyl]amino]ethyl]-1-(diphenylmethyl)-1H-indol-3-yl]propyl]benzoic acid (2) and 4-[2-[5-chloro-2-[2-[[[(3,4-dichlorophenyl)methyl]sulfonyl]-amino]ethyl]-1-(diphenylmethyl)-1H-indol-3-yl]ethoxy]benzoic acid (3).
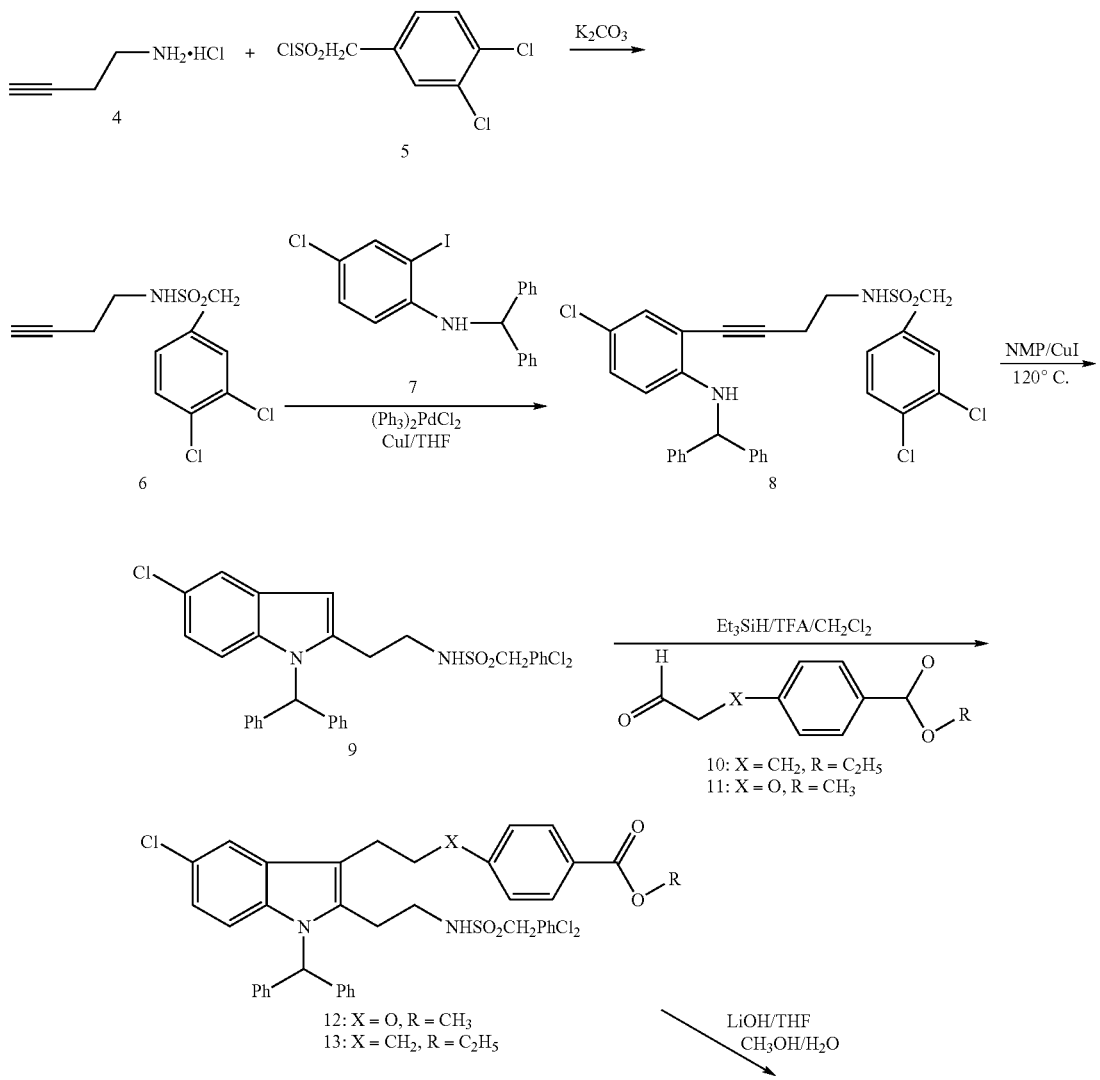

-continued

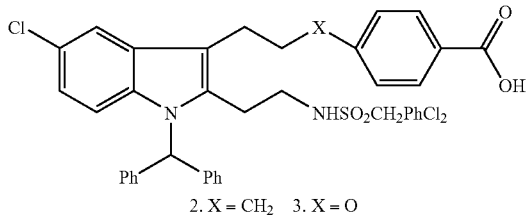

2. X = CH₂   3. X = O

In Scheme 2, the first intermediate (6) is coupled with benzhydryl-(4-chloro-2-iodophenyl)amine (7) with a catalytic amount of dichlorobis(triphenylphosphine)palladium (II) to give an arylalkyne derivative. Cyclization of this arylalkyne is performed in N-methyl-pyrrolidinone with catalytic amount of CuI to give corresponding indole (9) in two steps. These coupling and cyclization reactions are known as Sonogashira and Castro reactions and are mediated by catalytic palladium and copper salts. The indole (9) can be alkylated with the aldehyde (10) using the reagent combination triethylsilane and trifluoroacetic acid in dichloromethane to yield the ester (13). Compound (12) is produced when the indole (9) is alkylated with the aldehyde (11) under the same conditions, but the yield typically is smaller. Hydrolysis of the ester (13) under common basic conditions produces the compound (2), and the ester (12) may be hydrolyzed to produce the compound (3).

Other highly preferred embodiments of the present invention include a process comprising the reactions illustrated in Scheme 2 wherein in compounds 8, 10–13, and 2–3 in place of the 3,4-dichlorophenyl group is a 2,6-dimethylphenyl or 2-(trifluoromethyl)phenyl group.

The present invention provides a variety of new compounds. Examples of these new compounds include:
N-But-3-ynyl-1-(3,4-dichlorophenyl)methanesulfonamide,
N-{4-[2-(benzhydrylamino)-5-chlorophenyl]but-3-ynyl}-1-(3,4-dichlorophenyl)methanesulfonamide,
N-[2-(1-benzhydryl-5-chloro-1H-indol-2-yl)ethyl]-1-(3,4-dichlorophenyl)methanesulfonamide, and
ethyl 4-{3-[1-benzhydryl-5-chloro-2-(2-{[(3,4-dichlorobenzyl)sulfonyl]amino}ethyl)-1H-indol-3-yl]propyl}benzoate.

Other examples include:
N-But-3-ynyl-1-(2,6-dimethylphenyl)methanesulfonamide,
N-{4-[2-(benzhydrylamino)-5-chlorophenyl]but-3-ynyl}-1-(2,6-dimethylphenyl)methanesulfonamide,
N-[2-(1-benzhydryl-5-chloro-1H-indol-2-yl)ethyl]-1-(2,6-dimethylphenyl)methanesulfonamide,
ethyl 4-{3-[1-benzhydryl-5-chloro-2-(2-{[(2,6-dimethylbenzyl)sulfonyl]amino}ethyl)-1H-indol-3-yl]propyl}benzoate,
N-But-3-ynyl-1-(2-(trifluoromethyl)phenyl)methanesulfonamide,
N-{4-[2-(benzhydrylamino)-5-chlorophenyl]but-3-ynyl}-1-(2-(trifluoromethyl)phenyl)methanesulfonamide,
N-[2-(1-benzhydryl-5-chloro-1H-indol-2-yl)ethyl]-1-(2-(trifluoromethyl)phenyl)methane-sulfonamide, and
ethyl 4-{3-[1-benzhydryl-5-chloro-2-(2-{[(2-(trifluoromethyl)benzyl)sulfonyl]amino}ethyl)-1H-indol-3-yl]propyl}benzoate.

Unless the context dictates otherwise, the following terms have the meanings set forth below wherever they appear in this specification or the appended claims.

Halogen and halo- refer to F, Cl, Br and I. Alkyl refers to a saturated hydrocarbon substituent or group containing from one to twenty carbon atoms and having straight or branched chains. Alkenyl refers to a hydrocarbon substituent or group containing from one to twenty carbon atoms, at least one carbon-carbon double bond, and having straight or branched chains. Alkynyl refers to a hydrocarbon substituent or group containing from one to twenty carbon atoms, at least one carbon-carbon triple bond, and having straight or branched chains. Alkoxy refers to an alkyl group bonded to an oxygen atom by a single oxygen-carbon bond. Aryl refers to an unsaturated hydrocarbon ring system containing from one to three fused rings, in which each ring is composed of 5–7 atoms and has conjugated double bonds. Heteroaryl refers to an unsaturated ring system which differs form aryl in that at least one ring atom is nitrogen, oxygen or sulfur.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

Pharmaceutically acceptable esters can be formed from reaction with an alcohol, for example, a $C_1$–$C_6$ alkanol, when a compound of this invention contains an acidic moiety.

The following examples are presented to illustrate certain embodiments of the present invention, but should not be construed as limiting the scope of this invention.

EXAMPLE 1

N-But-3-ynyl-1-(3,4-dichlorophenyl)methanesulfonamide

To a mixture of potassium carbonate (40.2 g, 296 mmol) in water (50 mL) and THF (50 mL) at 15–20° C. was added but-3-ynylamine hydrogen chloride (10.4 g, 98.5 mmol). Then, (3,4-dichlorophenyl)methanesulfonyl chloride (5, 30.7 g, 118 mmol) was added in portions during of a period of 30 min. The mixture was stirred for 4 h at rt. THF is evaporated. The mixture is extracted with EtOAc (2×200 mL). The combined organic extracts were dried over $Na_2SO_4$. The solvent is evaporated to give a white solid (20.5 g, 71%). $^1$H NMR (CDCl$_3$): δ7.53 (d, 1H, J=2.0 Hz), 7.47 (d, 1H, J=4.2 Hz), 7.27 (m, 1H), 4.52 (t, 1H, J=6.2 Hz), 4.22 (s, 2H), 3.17 (dd, 2H, J=6.2 Hz, 12.5 Hz), 2.41 (m, 2H), 2.07 (m, 1H)

EXAMPLE 2

N-{4-[2-benzhydrylamino)-5-chlorophenyl]but-3-ynyl}-1-(3,4-dichlorophenyl)methanesulfonamide To a mixture of benzhydryl-(4-chloro-2-iodophenyl) amine (2.0 g, 4.76 mmol), dichlorobis(triphenylphosphine) palladium (II) (66.8 mg, 0.0952 mmol), copper (I) iodide (18.0 mg, 0.0952 mmol), and triethylamine (0.72 g, 7.14 mmol) was added N-but-3-ynyl-1-(3,4-dichlorophenyl) methanesulfonamide (1.67 g, 5.71 mmol). The mixture was stirred for 18 h at rt. Then, N-but-3-ynyl-1-(3,4-dichlorophenyl)methanesulfonamide (0.42 g) was added. The mixture was stirred for 3 hours. The solvent was evaporated. The residue was purified by column chromatography, using a mixture of heptane and EtOAc (3:1) as elute to give a white solid (2.20 g, 81%). $^1$H NMR (CDCl$_3$): δ7.2–7.6 (m, Ph, CHPh$_2$), 6.98 (m, 1H), 6.30 (d, 1H, J=8.9 Hz), 5.49 (d, 1H, J=4.6 Hz), 5.06 (d, 1H, J=4.5 Hz), 4.38 (t, 1H, J=6.24 Hz), 4.14 (s, 2H), 3.14 (dd, 2H, J=6.4, 12.6 Hz), 2.61 (t, 2H, J=6.3 Hz).

EXAMPLE 3

N-[2-(1-benzhydryl-5-chloro-1H-indol-2-yl)ethyl]-1-3,4-dichlorophenyl)methanesulfonamide A mixture of N-{4-[2-(benzhydrylamino)-5-chlorophenyl]but-3-ynyl}-1-(3,4-dichlorophenyl)-methanesulfonamide (1.0 g, 1.71 mmol) and copper (I) iodide (0.30 g, 1.58 mmol) was heated to 120° C. and stirred for 7 h, and then cooled to room temperature. Water (50 mL) was added. The mixture was extracted with EtOAc (2×50 mL). The combined organic extracts were dried over Na$_2$SO$_4$. The solvent was evaporated. The residue was purified by column chromatography, using a mixture of heptane and EtOAc (2:1) as elute to give a white solid (0.76 g, 76%). $^1$H NMR (CDCl$_3$): δ6.7–7.6 (m, Ph, CHPh$_2$), 6.58 (d, 1H, J=8.9 Hz), 4.20 (m, 1H), 3.99 (s, 2H), 3.10 (dd, 2H, J=6.9, 13.3 Hz), 2.94 (t, 2H, J=6.7 Hz).

EXAMPLE 4

Ethyl 4-{3-[1-benzhydryl-5-chloro-2-{[(3,4-dichlorobenzyl)sulfonyl]amino}ethyl)-1H-indol-3-yl] propyl}benzoate To a solution N-[2-(1-benzhydryl-5-chloro-1H-indol-2-yl)ethyl]-1-(3,4-dichlorophenyl)-methanesulfonamide (3.0 g, 5.14 mmol), triethylsilane (1.79 g, 15.4 mmol), and 4-(3-oxopropyl)benzoic acid ethyl ester (1.26 g, 6.16 mmol) in dichloromethane (30 mL) at −20 to −25° C. was added trifloroacetic acid (2.93 g, 25.7 mmol) during a period of 1 min. The mixture was warmed to −10° C. and stirred for 4 h. Saturated aqueous NaHCO$_3$ (20 mL) was added. The mixture was extracted with EtOAc (150 mL). The organic extract was dried over Na$_2$SO$_4$. The solvent is evaporated. The residue is purified by column chromatography, using a mixture of heptane and EtOAc (4:1) as elute to give a white solid (2.25 g, 56%). $^1$H NMR (CDCl$_3$): δ6.9–7.6 (m, Ph, CHPh$_2$), 7.97 (d, 1H, J=1.6 Hz), 7.41 (d, 1H, J=1.9 Hz), 6.50 (d, 1H, J=8.9 Hz), 4.35 (dd, 2H, J=7.1, 14.3 Hz), 4.13 (m, 1H), 3.92 (s, 2H), 2.95 (m, 2H), 2.71 (m, 6H), 1.96 (m, 2H), 1.38 (t, 3H, J=7.1 Hz).

EXAMPLE 5

4-[3-[5-chloro-2-[2-[[[(3,4-dichlorophenyl)-methyl]-sulfonyl]amino]ethyl]-1-(diphenylmethyl)-1H-indol-3-yl]propyl]benzoic acid A solution of ethyl 4-{3-[1-benzhydryl-5-chloro-2-(2-{[(3,4-dichlorobenzyl)sulfonyl]-amino}ethyl)-1H-indol-3-yl]propyl}benzoate (0.50 g, 0.65 mmol), LiOH (0.24 g, 10.0 mmol), methanol (5 mL), THF (5 mL) and water (5 mL) was stirred for 18 h at rt, then diluted with water (200 mL). 1 N HCl (10 mL) was added. The reaction mixture was extracted with EtOAc (2×50 mL). The organic extracts were dried over Na$_2$SO$_4$. The solvent is evaporated to give a white solid (0.46 g, 96%). $^1$H NMR (DMSO$_{d6}$): δ12.80 (br.s, 1H), 7.89 (d, 2H, J=2 Hz), 7.59 (d, 1H, J=1.5 Hz), 7.53 (d, 1H, J=6 Hz), 7.48 (d, 1H, J=1.5 Hz), 7.38 (m, 9H), 7.20 (m, 5H), 6.77 (dd, 1H, J=6.9 & 1.5 Hz), 6.46 (d, 1H, J=6.9 Hz), 4.36 (s, 2H), 3.18 (m,2H), 2.96 (m,2H), 2.76 (m, 4H), 1.90(m, 2H).

Many variations of the present invention not illustrated herein will occur to those skilled in the art. The present invention is not limited to the embodiments illustrated and described herein, but encompasses all the subject matter within the scope of the appended claims.

The invention claimed is:

1. A compound of the formula (II)

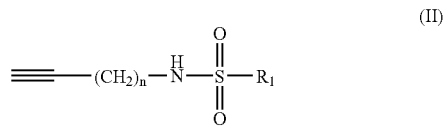

(II)

wherein n is an integer in the range of 0–10, and
R$_1$ is —CH$_2$-phenyl,
   wherein the phenyl ring is substituted with 1–2 substituents independently selected from the group consisting of C$_1$–C$_4$ alkyl, C$_1$–C$_4$ alkoxy, halogen, and nitrile,
      wherein each alkyl and alkoxy optionally is substituted with one to the maximum number of halogen atoms,
provided R$_1$ is not (2-chlorophenyl)methyl.

2. A compound according to claim 1, wherein n is an integer in the range of 0–4.

3. A compound according to claim 1, wherein n is 2.

4. A compound according to claim 1, wherein the phenyl ring is substituted by 1–2 substituents independently selected from the group consisting of C$_1$–C$_4$ alkyl, C$_1$–C$_4$ perhaloalkyl, and halogen.

5. A compound according to claim 4, wherein the phenyl ring is substituted by 1–2 substituents independently selected from the group consisting of CH$_3$, CF$_3$, and Cl.

6. A compound according to claim 1, wherein R$_1$ is selected from the group consisting of (3,4-dichlorophenyl) methyl, (2,6-dimethylphenyl)methyl, and (2-(trifluoromethyl)phenyl)methyl.

7. A compound selected from the group consisting of:
   N-But-3-ynyl-1-(3,4-dichlorophenyl)methanesulfonamide,
   N-But-3-ynyl-1-(2,6-dimethylphenyl)methanesulfonamide, and
   N-But-3-ynyl-1-(2-(trifluoromethyl)phenyl)methanesulfonamide.

8. A process for making a compound of Formula (II)

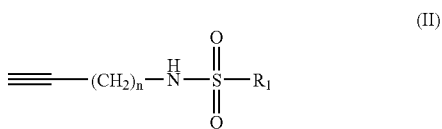

(II)

wherein n is an integer in the range of 0–10, and
R$_1$ is —CH$_2$-phenyl;
    wherein the phenyl ring is substituted with 1–2 substituents independently selected from the group consisting of C$_1$–C$_4$ alkyl, C$_1$–C$_4$ alkoxy, halogen, and nitrile,
    wherein each alkyl and alkoxy optionally is substituted with one to the maximum number of halogen atoms,
provided R$_1$ is not (2-chlorophenyl)methyl,
said process comprising reacting a compound having the formula

with a compound having the formula

or a salt form thereof in a solvent and in the presence of a base.

9. The process according to claim 8, wherein n is an integer in the range of 0–4.

10. The process according to claim 9, wherein n is 2.

11. The process according to claim 8, wherein the phenyl ring is substituted by 1–2 substituents independently selected from the group consisting of C$_1$–C$_4$ alkyl, C$_1$–C$_4$ perhaloalkyl, and halogen.

12. The process according to claim 11, wherein the phenyl ring is substituted by 1–2 substituents independently selected from the group consisting of CH$_3$, CF$_3$, and Cl.

13. The process according to claim 11, wherein R$_1$ is selected from the group consisting of (3,4-dichlorophenyl)methyl, (2,6-dimethylphenyl)methyl, and (2-(trifluoromethyl)phenyl)methyl.

14. The process according to claim 8, wherein the base comprises potassium carbonate.

15. The process according to claim 8, wherein the solvent comprises tetrahydrofuran.

16. The process according to claim 8, wherein the solvent comprises a mixture of tetrahydrofuran and water.

17. The process according to claim 8, wherein R$_1$—SO$_2$Cl is reacted with a hydrochloric acid salt of HC≡C(CH$_2$)$_n$NH$_2$.

* * * * *